United States Patent [19]

Jones

[11] Patent Number: 5,498,415
[45] Date of Patent: Mar. 12, 1996

[54] DISINFECTANT FOR THE TREATMENT OF WATER SYSTEMS

[75] Inventor: Ronald L. Jones, Norcross, Ga.

[73] Assignee: Bio-Lab, Inc., Decatur, Ga.

[21] Appl. No.: 234,638

[22] Filed: Apr. 28, 1994

Related U.S. Application Data

[63] Continuation of Ser. No. 898,293, Jun. 15, 1993, abandoned, which is a continuation of Ser. No. 652,983, Feb. 11, 1991, abandoned.

[51] Int. Cl.⁶ .................................................. A01N 25/08
[52] U.S. Cl. ........................ 424/409; 424/405; 424/76.1; 424/661; 424/723
[58] Field of Search .................... 424/405, 76.1, 424/661, 723, 409, 489, 661, 665

[56] References Cited

U.S. PATENT DOCUMENTS

| | | | |
|---|---|---|---|
| 3,165,521 | 1/1965 | Slezak et al. | 260/256.4 |
| 4,382,799 | 5/1983 | Davis et al. | 8/107 |
| 4,997,450 | 3/1991 | Olson et al. | 8/109 |
| 5,000,869 | 3/1991 | Dittert | 252/174.13 |
| 5,015,643 | 5/1991 | Jones et al. | 574/241 |

FOREIGN PATENT DOCUMENTS 0403465  12/1990  European Pat. Off. .......... C02F 1/76

*Primary Examiner*—Thurman K. Page
*Assistant Examiner*—Neil Levy
*Attorney, Agent, or Firm*—Woodard, Emhardt, Naughton, Moriarty & McNett

[57] ABSTRACT

Disclosed are solid oxidizer compositions that provide either hypochlorous or hypobromous acid for disinfecting water systems comprising either of the following mixtures: (a) approximately 50–99.99% by weight of trichloro-s-triazinetrione and 0.01–50% by weight of glycolurils of the following structure:

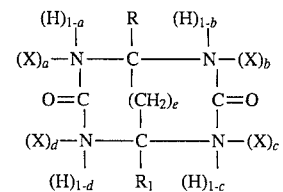

wherein R and $R_1$ are members selected from the group consisting of hydrogen, lower alkyl radicals of from 1–4 carbon atoms and phenyl, and X is selected from the group consisting of hydrogen, chlorine and bromine and a, b, c, d and e are integers of from 0–1;

and (b) approximately 50–99.99% by weight of trichloro-s-triazinetrione, 0.01–50% by weight of glycolurils of the above structure (a) and 0–20% by weight of an alkali bromide salt.

14 Claims, No Drawings

DISINFECTANT FOR THE TREATMENT OF WATER SYSTEMS

This application is a continuation of application Ser. No. 07/898,293, filed Jun. 15, 1993, now abandoned, which is a continuation of application Ser. No. 07/652,983, filed Feb. 11, 1991, now abandoned.

FIELD OF THE INVENTION

This invention relates to solid oxidizer compositions that provide either hypochlorous or hypobromous acid for disinfecting water systems, such as swimming pools, spas, decorative fountains, recirculating water cooling systems, health related baths, dehumidifier systems, ponds and reservoirs.

BACKGROUND

A number of different compositions and methods that provide hypobromous or hypochlorous acid for disinfecting water systems have been utilized. These technologies currently in use have some serious deficiencies. Trichloro-s-triazinetrione (T.C.C.A.) can be pressed into a solid composition such as a stick, tablet or puck and placed in an erosion feeder, skimmer, or a floating slow release device. However, for a number of applications these solid compositions erode too rapidly. In some cases they do not maintain their integrity as water is circulated through the release device. Consequently, the disinfectant splits, cracks and breaks into small pieces. These small pieces expose more surface area and increased erosion occurs. The disinfectant is released too rapidly and is not satisfactory for the treatment of most water systems. This is also true of blended compositions containing T.C.C.A. and sodium bromide. An example blend contains 96% T.C.C.A., 2% sodium bromide and 2% inert. In other cases as the water temperature increases the erosion rate of the disinfectant increases. The disinfectant is then released too rapidly into the water system and is not satisfactory for treatment of most water systems.

PRIOR ART

The process for the preparation of glycoluril is disclosed in U.S. Pat. No. 2,731,472 (Reibnitz). U.S. Pat. No. 3,071,591 (Paterson) discloses a method for the preparation of N-halogenated glycolurils containing both bromine and chlorine for use as disinfecting agents. The use of haloglycolurils for the sanitizing agent in swimming pools is disclosed in U.S. Pat. No. 3,165,521 (Lezak). The use of polyhaloglycolurils for controlling algae in water is disclosed in U.S. Pat. No. 3,252,901 (Zettler). The use of chlorinated glycolurils in the treatment of sewage is disclosed in U.S. Pat. No. 3,445,383 (Horvath et al).

The use of substituted glycolurils in combination with trichlorocyanuric acid and sodium stearate in sanitizing sticks is disclosed in U.S. Pat. No. 3,342,674 (Kowalski). Use of chlorinated glycolurils in combination with a metallic hypochlorite in treating sewage is disclosed in U.S. Pat. No. 3,629,408 (Horvath). U.S. Pat. No. 3,187,004 (Slezak) discloses the synthesis of alkyl and aryl substituted glycoluril and their use in sanitizing swimming pools. This patent discloses the use of these N-halogenated glycolurils with alkaline metal salts.

SUMMARY OF THE INVENTION

It is an object of the present invention to provide solid oxidizer compositions that provide either hypochlorous or hypobromous acid for use in slow release feeders or skimmers for disinfecting water systems which will dissolve at a relatively slow rate so that the disinfectant will be released uniformly into the water system over an extended period of time.

These objects have been obtained by developing solid oxidizer compositions to provide either hypochlorous or hypobromous acid for disinfecting water systems comprising either of the following mixtures: (a) approximately 50–99.99% by weight of trichloro-s-triazinetrione and 0.01–50% by weight of glycolurils of the following structure:

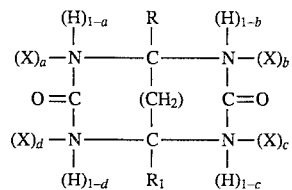

wherein R and $R_1$ are members selected from the group consisting of hydrogen, lower alkyl radicals of from 1–4 carbon atoms and phenyl, and X is selected from the group consisting of hydrogen, chlorine and bromine and a, b, c, d and e are integers of from 0–1;

and (b) approximately 50–99.99% by weight of trichloro-s-triazinetrione, 0.01–50% by weight of glycolurils of the above structure (a) and 0–20% by weight of an alkali bromide salt.

It is a further object of the present invention to provide a blue pigment for these oxidizer compounds so they can be identified as a disinfectant when it is in its dry form. It is a further object of this invention that the pigment not be stable in the water system so that it does not stain the walls of the swimming pools and spas. It has been found that the pigment lazurite is stable when mixed in dry form with these oxidizers used for disinfecting water systems. It has also been found that this pigment is not stable in the water system with certain oxidizers so that the water remains clear in color and does not stain the walls of pools and spas.

These compositions are blended together and formed or compressed into solid forms, such as tablets, sticks, pucks or other shapes. The disinfectant can then be placed in a release device through which water is circulated to disinfect a water system, such as a swimming pool or cooling tower. In the case of a swimming pool, the tablet, stick or puck can be placed into a skimmer basket.

The disinfectants of this invention dissolve at a slower rate in a release device than comparable compositions containing only T.C.C.A. or T.C.C.A./NaBr compositions. Consequently, the disinfectant of this invention adds hypochlorous or hypobromous acid to a water system at a controlled and uniform rate over a longer period of time.

DESCRIPTION OF THE INVENTION

This invention produces a solid disinfectant that dissolves at a slow and relatively uniform rate when used in a release device for water systems. The disinfectant can be any of the following mixtures: (a) approximately 50–99.99% by weight of trichloro-s-triazinetrione and 0.01–50% by weight of glycolurils of the following structure:

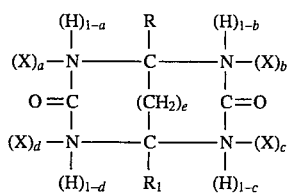

wherein R and $R_1$ are members selected from the group consisting of hydrogen, lower alkyl radicals of from 1–4 carbon atoms and phenyl, and X is selected from the group consisting of hydrogen, chlorine and bromine and a, b, c, d and e are integers of from 0–1; (X may be the same or different halogens or a combination of hydrogen and one or more halogens. R and $R_1$ may be the same or different radicals. It is preferred that R and $R_1$ be either hydrogen or methyl. Alkyl radicals with longer length render the glycolurils less soluble in water.);
and (b) approximately 50–99.99% by weight of trichloro-s-triazinetrione, 0.01–50% by weight of glycolurils of the above structure (a) and 0–20% by weight of an alkali bromide salt.

The disinfectant which contains the alkali metal bromide salt is used if it is desired to provide hypobromous acid. A preferred composition is from 80–98% trichloro-s-triazinetrione (T.C.C.A.) and 2–20% of a glycoluril or from 70–90% trichloro-s-triazinetrione (T.C.C.A.) and from 5–10% of sodium or potassium bromide salt and from 5–20% of a glycoluril. Another preferred mixture is from 75–90% trichloro-s-triazinetrione and from 5–10% potassium bromide and from 5–20% of a glycoluril. The glycoluril can be used with T.C.C.A. alone or in combination with a sodium or potassium bromide salt as indicated above. The preferred glycolurils are glycoluril and the chloroglycolurils, such as dichloroglycoluril and tetrachloroglycoluril. For most applications glycoluril is preferred. The T.C.C.A. is available from Monsanto Chemical Co. under the name ACL-90.

This invention also provides a blue pigment for these disinfectants, with the pigment being stable in the dry form. When certain disinfectants are added to a water system, the pigment decomposes so that the water is not colored which would result in staining the walls of swimming pools and spas.

A chlorine stable pigment has been found which is stable in dry form with the above disinfectants. This pigment is ultramarine blue or lazurite, commonly sold under the trade name Pylam Pylaklor Dry Blue™* S-726 (Pigment Blue 29; CI 77007). It has the following composition [(Na, Ca)$_4$ (AlSi O$_4$)$_3$ (SO$_4$, S, Cl)] or [Ca$_2$Na$_6$ (Al$_6$(SiO$_4$)$_6$SO$_4$ S] or [Na$_5$ (Al$_3$(SiO$_4$)$_3$S] or [Na$_5$ (Al$_3$(SiO$_4$)$_3$S) (Cl). This pigment is blue, blue-violet or greenish-blue in color. Lazurite is oxidizer stable so that the solid composition is blue in color. Lazurite is decomposed by the disinfectant in the water systems. Decomposition of the pigment in the water system is preferred because otherwise the pigment may result in a slight blue tint in the water. This is important for some applications as pigment might be objectionable to users of certain water systems such as swimming pools.

*Trademark of Pylam Products Company, Inc.

The lazurite is added to the disinfectant in an amount of from 0.01–0.5% by weight. It is preferred that it be present in an amount of 0.05–0.25% by weight. The preferred glycolurils include glycoluril and the chloroglycolurils, such as dichloroglycoluril and tetrachloroglycoluril, in combination with the lazurite. The lazurite is added to the oxidizer by simple mixing.

The lazurite pigment gives a distinctive blue color to the white disinfectants which is stable for a long period of time. However when the pigmented disinfectant is introduced into the water system, the pigment becomes unstable with certain disinfectants so the water is not colored blue. This is preferred to avoid staining the walls of swimming pools and spas.

It is also possible for the formulation to include a filler. The filler is an inert substance, such as sodium chloride or boric acid, that can be used to assist in the tabletting process. A filler can be used in any concentration provided the composition contains the required amount of the disinfectant. The filler is preferably present from 0.05–10% by weight.

In addition to the components of the disinfectant described above, the formulation may also contain other ingredients such as tabletting aids, e.g., mold release agents, binders, corrosion inhibitors, scale inhibitors and other components known to one skilled in the art. The tablets, sticks or pucks are formed or compressed into solid form. They can be compressed by a hydraulic or mechanical press.

It is preferred that the disinfectant of this invention be used in a release device so that the disinfectant is immersed or partially immersed in water within an enclosure in which the disinfectant is gradually eroded and either hypochlorous or hypobromous acid are released to disinfect that water system. It can also be used in in-line feeders, floaters, off-line chlorinators or skimmers. The preferred device is a skimmer.

As illustrated in the following examples, the disinfectants of this invention dissolve at a slower rate in a release device than comparable compositions containing only trichloro-s-triazinetrione (T.C.C.A.). Consequently the disinfectant of this invention adds hypochlorous or hypobromous acid to a water system at a controlled and uniform rate over a long period of time.

The solid disinfectants of this invention are useful in disinfecting water systems such as swimming pools, spas, hot tubs and cooling towers. These compositions are normally formed or pressed into tablets, sticks, pucks or other shapes and placed in a release device such as an erosion feeder, skimmer, in-line halogenator or floating release device in the system.

Structurally the compound glycoluril has the following formula:

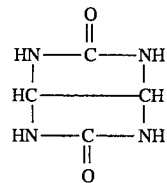

EXAMPLE 1

A pilot batch of the solid disinfectant was prepared adding 270 pounds of T.C.C.A. and 30 pounds of glycoluril into a V-shaped tumble blender. The batch was blended for five minutes. Part of this composition was pressed into one inch tablets using a mechanical press applying approximately 15,000 pounds of pressure. The rest of the batch was pressed into 4.5 inch 227 gm sticks using a hydraulic press applying 35,000 pounds of pressure. Erosion studies were conducted on the one inch tablets using an erosion control device through which water is circulated at a controlled rate of flow (gallons per hour, gph). These one inch tablets were compared to one inch tablets containing 100% T.C.C.A. which were produced in the same manner.

The one inch tablets were placed in an erosion control device. The water temperature was maintained at 80° F., and the flow rate was 20 gallons per hour. After 48 hours the tablets containing T.C.C.A. and glycoluril retained 87% of its initial weight. The tablet that contained 100% T.C.C.A. only retained 58% of its initial weight. The addition of the glycoluril resulted in 3 fold reduction in the erosion rate.

Erosion studies were also conducted on the 227 gm stick using a device that simulates a swimming pool skimmer. In this device three sticks can be tested simultaneously under identical conditions. Water temperature was 80° F., and the flow rate was 600 gallons per hour. After 72 hours the stick containing the glycoluril retained 75% of its initial weight while the stick containing 100% T.C.C.A. only retained 9% of its weight.

The stick containing the glycoluril retained 83% of its weight after 48 hours while the stick containing 100% T.C.C.A. only retained 31% of its weight. After 24 hours the glycoluril containing stick retained 92% of its weight while the T.C.C.A. stick only retained 66% of its weight.

EXAMPLE 2

Tablets one inch in diameter and weighing 15 gm were prepared in the laboratory by mixing the ingredients and pressing using a 30 ton Carver hydraulic lab press, applying 15,000 pounds of pressure for 20 seconds. One set of tablets was prepared containing 90% T.C.C.A. and 10% glycoluril. The other set of tablets contained 95% T.C.C.A. and 5% glycoluril. The erosion rates of these tablets were compared to tablets containing 100% T.C.C.A. The erosion testing was conducted using the same erosion control device used in Example 1. Water temperature was maintained at 80° F. with a flow rate of 20 gallons per hour. The weights of the tablets were checked after 72 hours. The tablet containing 90% T.C.C.A. and 10% glycoluril retained 88% of its initial weight after 72 hours while the tablet containing 95% T.C.C.A. and 5% glycoluril retained 76% of its weight after 72 hours. The tablet with 100% T.C.C.A. only retained 52% of its initial weight after 72 hours.

EXAMPLE 3

To test the uniformity of the product from a pilot batch produced in Example 1, erosion studies were conducted on eight one inch tablets containing 90% T.C.C.A. and 10% glycoluril. The erosion rates were obtained using the same erosion testing device as was used in Example 1. Water temperature was maintained from 50°–55° F. with water circulating at a flow rate of 20 gallons per hour. After eight days the tablets retained the percentage of weight set forth in the Table below.

| Tablet # | % Weight Retention after 8 Days |
| --- | --- |
| 1 | 82% |
| 2 | 83% |
| 3 | 82% |
| 4 | 79% |
| 5 | 81% |
| 6 | 81% |
| 7 | 83% |
| 8 | 82% |

As can be seen from the above table, the addition of 10% glycoluril results in very high weight retention over a period of eight days. All the tablets maintained their integrity. The average weight retention rate for the eight tablets was 82%. All eight tablets were within 3% of the average weight which indicates a consistently blended product from the pilot batch.

EXAMPLE 4

One inch tablets were prepared in the laboratory by mixing the ingredients and pressing using a thirty ton Carver hydraulic lab press. The tablets contained the materials set forth in the Table below. The erosion rates of the tablets were compared using the same erosion testing device as used in Example 1. The water temperature was maintained at 80° F., and the flow rate was 20 gallons per hour.

| Composition Tested | % Weight Retention after 48 Hours |
| --- | --- |
| 1. 75% T.C.C.A., 5% potassium bromide, 20% glycoluril | 94% |
| 2. 100% T.C.C.A. | 54% |

EXAMPLE 5

Tablets containing 75% T.C.C.A., 5% potassium bromide, 20% glycoluril were prepared in the laboratory by mixing the ingredients and pressing using a 30 ton Carver hydraulic lab press. The ingredients were pressed into one inch tablets weighing 15 gm. All tablets were pressed at 15,000 pounds pressure for twenty seconds. The erosion rates of these tablets were compared with one inch 15 gm tablets containing 96% T.C.C.A. and 4% sodium bromide which were prepared in the same way. The erosion rates of these tablets were compared by placing them in an erosion control device through which water was circulated at a controlled rate. Water was circulated at the same rate over all the tablets. Water temperature was maintained at 60°–70° F. Water was allowed to flow over the tablets for one hour at which time they were mopped dry and weighed. The tablets were then returned to the feeder and water was allowed to flow over the tablets for 48 hours after the initial wetting. The tablets were then removed, mopped dried and reweighed. The percent weight retention was calculated. The various formulations are set forth below. The abbreviation T.C.C.A. is used for the trichloro-s-triazinetrione.

| Composition Tested | % Weight Retention after 48 Hours |
| --- | --- |
| 75% T.C.C.A., 5% KBr, 20% glycoluril | 94% |
| 96% T.C.C.A., 4% NaBr | 21% |

EXAMPLE 6

Tablets one inch in diameter and weighing 15 gm were prepared in the laboratory by mixing the ingredients and pressing into tablets using a thirty ton Carver hydraulic laboratory press. The ingredients were pressed into tablets by applying 15,000 pounds of pressure for 20 seconds. One set of tablets was prepared containing 90% T.C.C.A. and 10% tetrachloroglycoluril (TCGU). A second set of tablets was prepared containing 95% T.C.C.A. and 5% tetrachloroglycoluril (TCGU). A third set of one inch 15 gm tablets were prepared containing 90% T.C.C.A. and 10% tetrabromoglycoluril (TBGU). The erosion rates of these tablets were compared to one inch tablets prepared in the same way containing 100% T.C.C.A. The erosion test was conducted using the same apparatus and methods used in Example 1. The water temperature was maintained at 80° F. with a flow rate of twenty gallons per hour. The weight of the tablets was determined after a twenty-four hour test period. The test results are summarized below:

| Blends/Tested | % Weight Retention After 24 Hours |
| --- | --- |
| TCCA 90%/TCGU 10% | 93% |
| TCCA 90%/TBGU 10% | 83% |
| TCCA 100% | 66% |
| TCCA 95%/TCGU 5% | 89% |

EXAMPLE 7

Tablets one inch in diameter and weighing 15 grams were prepared in the laboratory by hand mixing the ingredients and then pressing using a 30 ton Carver hydraulic lab press applying 15,000 lbs of pressure for 20 seconds. The tablets contained glycoluril in amounts ranging from 0.25% to 10.0% and the balance of the formulation was T.C.C.A. The erosion rate of the tablets was determined using the erosion testing device from Example 1. The tablets were compared to tablets containing 100% TCCA. The water temperature was maintained at 80° F. with a flow rate of 20 gph. The percent weight retention (% WRT) was determined at 24, 48 and 72 hours.

RESULTS

| TABLETS # | % GLYCOLURIL | % TCCA | 24 HRS. | % WRT 48 HRS. | 72 HRS. |
| --- | --- | --- | --- | --- | --- |
| 1 | 0 | 100.00 | 78.0 | 58.0 | 41.0 |
| 2 | 0.25 | 99.75 | 79.0 | 61.0 | 43.0 |
| 3 | 0.50 | 99.50 | 79.0 | 60.0 | 43.0 |
| 4 | 1.00 | 99.00 | 80.0 | 61.0 | 45.0 |
| 5 | 1.50 | 98.50 | 81.0 | 63.0 | 48.0 |
| 6 | 2.00 | 98.00 | 82.0 | 64.0 | 49.0 |
| 7 | 3.00 | 97.00 | 81.0 | 65.0 | 50.0 |
| 8 | 4.00 | 96.00 | 83.0 | 68.0 | 55.0 |
| 9 | 5.00 | 95.00 | 83.0 | 72.0 | 60.0 |
| 10 | 10.00 | 90.00 | 91.0 | 85.0 | 81.0 |

This example illustrates that as little as 0.25% glycoluril reduces the erosion rate of TCCA. As the amount of glycoluril is increased, the erosion rate is decreased.

EXAMPLE 8

This example illustrates the ability of other alkyl and phenyl derivatives to reduce the erosion rate of TCCA. Tablets one inch in diameter and weighing 15 grams were prepared in the laboratory by mixing the ingredients and pressing into tablets using a thirty ton Carver hydraulic laboratory press. The ingredients were pressed into tablets by applying 15,000 pounds of pressure for 20 seconds. The tablet compositions were

| | | |
| --- | --- | --- |
| 1. | 95.0% TCCA/5.0% Diethymglycoluril | (DEGU) |
| 2. | 95.0% TCCA/5.0% EthylMethylglycoluril | (EMGU) |
| 3. | 95.0% TCCA/5.0% Dimethylglycoluril | (DMGU) |
| 4. | 95.0% TCCA/5.0% Diphenylglycoluril | (DPGU) |

The erosion rates of these tablets were compared to one inch 100% TCCA tablets prepared in the same manner. The erosion test was conducted using the same apparatus and methods used in Example 1. The water temperature was maintained at 80° F. with a flow rate of twenty gallons per hour.

The percent weight retention (%WRT) was obtained 24, 48 and 72 hours. The test results are summarized below:

| | % W.R.T | | |
| --- | --- | --- | --- |
| TEST BLENDS | 24 hrs. | 48 hrs. | 72 hrs |
| 1. TCCA 95%/DEGU 5% | 82.0 | 68.0 | 56.0 |
| 2. TCCA 95%/EMGU 5% | 82.0 | 69.0 | 57.0 |
| 3. TCCA 95%/DMGU 5% | 83.0 | 70.0 | 58.0? |
| 4. TCCA 95%/DPGU 5% | 89.0 | 81.0 | 74.0 |
| 5. TCCA 100% | 77.0 | 58.0 | 40.0 |
| 6. TCCA 95%/Glycoluril 5% | 83.0 | 72.0 | 60.0 |

EXAMPLE 9

The example illustrates the stability of lazurite blue pigment with halogenated glycolurils. Samples containing 0.2% lazurite and 99.8% of either tetrachloroglycoluril or tetrabromoglycoluril and 10% tetrachloroglycoluril and 90% trichloro-s-triazinetrione were blended until a uniform blue color was obtained. These samples were stored at 50° F. for days. The stability of the blue pigment in the compositions was observed visually at the end of the storage period. The following results were obtained for each sample.

TABLE I

| | DAY 1 | DAY 30 | STABILITY OF PIGMENT |
| --- | --- | --- | --- |
| 1. Tetrachloroglycoluril | Blue | Blue | Stable |
| 2. Tetrabromoglycoluril | Blue | Blue | Stable |
| 3. A mixture of 10% by weight of tetrachloroglycoluril and 90% by weight of trichloro-s-trione | Blue | Blue | Stable |
| 4. A mixture of 5% by weight of glycoluril and 90% trichloro-s-trione and 5% | Blue | Blue | Stable |

TABLE I-continued

| | DAY 1 | DAY 30 | STABILITY OF PIGMENT |
|---|---|---|---|
| potassium bromide | | | |

I claim:

1. A solid disinfecting composition in the form of a tablet, stick or puck consisting essentially of a mixture of:
   a. 50–99% by weight of trichloro-s-triazinetrione;
   b. 0.01–50% by weight of glycolurils having the structure:

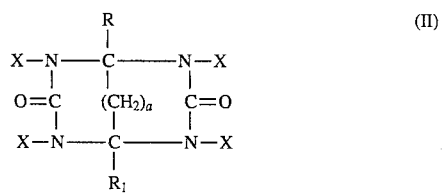

in which R and $R_1$ are independently selected from the group consisting of hydrogen, lower alkyl radicals of from 1 to 4 carbon atoms, and phenyl; each X is hydrogen; and a is either 0 or 1; and
   c. about 5–20% by weight of an alkali bromide salt selected from the group consisting of sodium bromide and potassium bromide,
   said composition providing a controlled and uniform rate of release of hypobromous or hypochlorous ion to a water system.

2. The composition of claim 1 in which the composition consists essentially of a mixture of trichloro-s-triazinetrione, glycoluril and sodium bromide, and in which R, $R_1$ and X are hydrogen and a is 0.

3. The composition of claim 2 in which the composition consists essentially of 70–90% trichloro-s-triazinetrione, 5–20% glycoluril, and 5–10% sodium bromide salt.

4. The composition of claim 1 in which the composition consists essentially of a mixture of trichloro-s-triazinetrione, glycoluril and potassium bromide, and in which R, $R_1$ and X are hydrogen and a is 0.

5. The composition of claim 4 in which the composition consists essentially of 70–90% trichloro-s-triazinetrione, 5–20% glycoluril, and 5–10% potassium bromide salt.

6. The composition of claim 1 and which includes less than about 20% glycoluril.

7. The composition of claim 6 and which includes less than about 10% glycoluril.

8. A method for providing prolonged release of hypobromous ion or hypochlorous ion into a water system which comprises the steps of:
   a. providing a solid disinfecting composition in the form of a tablet, stick or puck consisting essentially of a mixture of 50–99.99% by weight of trichloro-s-triazinetrione; 0.01–50% by weight of glycolurils having the structure:

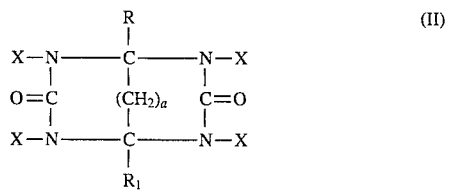

in which R and $R_1$ are independently selected from the group consisting of hydrogen, lower alkyl radicals of from 1 to 4 carbon atoms, and phenyl; each X is hydrogen; and a is either 0 or 1; and about 5–20% by weight of an alkali bromide salt selected from the group consisting of sodium bromide and potassium bromide, said composition providing a controlled and uniform rate of release of hypobromous or hypochlorous ion to a water system; and
   b. contacting the tablet, puck or stick with the water to obtain a controlled and uniform rate of release of hypobromous or hypochlorous to the water.

9. The method of claim 8 in which the composition consists essentially of a mixture of trichloro-s-triazinetrione, glycoluril and sodium bromide, and in which R, $R_1$ and X are hydrogen and a is 0.

10. The method of claim 9 in which the composition consists essentially of 70–90% trichloro-s-triazinetrione, 5–20% glycoluril, and 5–10% sodium bromide salt.

11. The method of claim 8 in which the composition consists essentially of a mixture of trichloro-s-triazinetrione, glycoluril and potassium bromide, and in which R, $R_1$ and X are hydrogen and a is 0.

12. The method of claim 11 in which the composition consists essentially of 70–90% trichloro-s-triazinetrione, 5–20% glycoluril, and 5–10% potassium bromide salt.

13. The composition of claim 8 and which includes less than about 20% glycoluril.

14. The composition of claim 8 and which includes less than about 10% glycoluril.

* * * * *